US008278291B1

(12) United States Patent
Wieland et al.

(10) Patent No.: US 8,278,291 B1
(45) Date of Patent: Oct. 2, 2012

(54) TREATMENT OF WRINKLES AND STRIAS WITH 4-HYDROXYANDROSTENEDIONE OR A DERIVATIVE THEREOF

(75) Inventors: Heinrich Wieland, St. Peter (DE); Alfred Schmidt, Hamburg (DE)

(73) Assignee: Curadis GmbH, Erlangen (DE)

( * ) Notice: Subject to any disclaimer, the term of this patent is extended or adjusted under 35 U.S.C. 154(b) by 0 days.

(21) Appl. No.: 10/049,968

(22) PCT Filed: Jul. 28, 2000

(86) PCT No.: PCT/EP00/07315
§ 371 (c)(1),
(2), (4) Date: Feb. 13, 2002

(87) PCT Pub. No.: WO01/12206
PCT Pub. Date: Feb. 22, 2001

(30) Foreign Application Priority Data

Aug. 13, 1999 (DE) .................................. 199 38 421

(51) Int. Cl.
*A61K 31/56* (2006.01)
(52) U.S. Cl. .................. 514/178; 514/177; 514/169
(58) Field of Classification Search .................. 514/172, 514/169, 177, 178
See application file for complete search history.

(56) References Cited

U.S. PATENT DOCUMENTS

| | | | | | |
|---|---|---|---|---|---|
| 5,254,594 | A | * | 10/1993 | Niikura et al. ............... | 514/648 |
| 5,280,035 | A | | 1/1994 | Bohlmann et al. ............ | 514/383 |
| 5,494,899 | A | | 2/1996 | Kincade et al. .................. | 514/21 |
| 5,770,609 | A | * | 6/1998 | Grainger et al. ............... | 514/319 |
| 5,906,987 | A | | 5/1999 | Chwalisz et al. ............. | 514/177 |
| 5,945,109 | A | * | 8/1999 | Schmidt et al. ............... | 424/401 |
| 5,972,921 | A | | 10/1999 | Santti et al. ................... | 514/177 |
| 6,020,327 | A | * | 2/2000 | Messenger ..................... | 514/170 |
| 6,071,526 | A | * | 6/2000 | Schmidt et al. ............... | 424/401 |
| 6,455,517 | B1 | * | 9/2002 | Tanabe et al. ................. | 514/182 |
| 6,471,972 | B1 | * | 10/2002 | Bonte et al. ................... | 424/401 |
| 6,641,848 | B1 | * | 11/2003 | Bonte et al. ................... | 424/757 |
| 6,920,883 | B2 | * | 7/2005 | Bessette et al. ............... | 128/898 |
| 2003/0211177 | A1 | * | 11/2003 | Pineda .......................... | 424/727 |

FOREIGN PATENT DOCUMENTS

| | | |
|---|---|---|
| DE | 33 38 212 A1 | 4/1985 |
| EP | 0 684 235 A1 | 11/1995 |
| EP | 0 776 661 A1 | 6/1997 |
| WO | WO 91/00731 | 1/1991 |
| WO | WO 92/18132 | 10/1992 |
| WO | WO 96/08231 | 3/1996 |
| WO | WO 97/36570 | 10/1997 |
| WO | WO 99/62459 | 12/1999 |
| WO | WO 99/62480 | 12/1999 |
| WO | WO 9962481 A1 * | 12/1999 |

OTHER PUBLICATIONS

Fritz et al. "Tamoxifen attenuates the effects of exogenous glucocorticoids on bone formation and growth in piglets" Endocrinology (1998) 139(8): 3399-3403.*
Webster's II New Riverside Dictionary (1994) (Houghton-Mifflin: Boston, MA) pp. 134 and 626.*
Taber's Cyclopedic Medical Dictionary. Thomas, C. ed. 15th Ediction (1985) (F.A. David: Philadelphia, PA), p. 1570-1571.*
Machine English language translation of the Description for WO 97/36570 by the EPO http://epo.worldlingo.com downloaded on Jun. 24, 2009.*
Machine English language translation of the Claims for WO 97/36570 by the EPO http://epo.worldlingo.com downloaded on Jun. 24, 2009.*
Varila et al. British J. Obstetrics and Gynocology (1995) 102: 985-989.*
Brincat et al. Maturitas (1987) 9(1): 1-5.*
Welzel et al. Tetrahedron (1985) 41(20); 4509-4517.*
Affinito et al. Maturitas (1999) 33: 239-247.*
Fujimoto et al. J. Am. Chem. Soc. (1982) 104: 4718-4720.*
Islam et al. Nutritional Neuroscience (2008) 11: 251-262.*
Brincat et al. British Medical Journal (1983) 287: 1337-1338.*
Marsh et al. J. Med. Chem. (1985) 28:788-795.*
Thesen, E., "Formestan, ein neuer Aromatase-Inhibitor", Pharmazeutische Zeitung, 141(26):32-40 (1996).
XP-002161790, Morita, K., et al., "Effect of Soybean Isoflavone on Bone Metabolism", Chemical Abstract Service, Columbus, OH. Database Chemlab Online.
Tanaka et al., "1,25-Dihydroxyvitamin $D_3$ Enhances the Enzymatic Activity and Expression of the Messenger Ribonucleic Acid for Aromatase Cytochrome P450 Synergistically with Dexamethasone Depending on the Vitamin D Receptor Level in Cultured Human Osteoblasts", *Endocrinology*, 137(5):1860-1869 (1996).
Neugarten, et al., "Estradiol Suppresses Mesangial Cell Type I Collagen Synthesis via Activation of the MAP Kinase Cascade", *American Physiological Society*, pp. F875-F881 (1999).
Stanczyk, et al., "Androstenedione is an Important Precursor of Dihydrotestosterone in the Genital Skin of Women and is Metabolized via 5☐-Androstanedione", *J. Steroid Biochem. Molec. Biol.*, 37(1):129-132 (1990).
You, et al., "Three Different Turkey Luteinizing Hormone Receptor (tLH-R) Isoforms I: Characterization of Alternatively Spliced tLH-R Isoforms and Their Regulated Expression in Diverse Tissues", *Biology of Reproduction*, 62:108-116 (2000).
Libby, P., "Changing Concepts of Atherogenesis", *Journal of Internal Medicine*, 247:349-358 (2000).
Labrie, et al., "Physiological Changes in Dehydroepiandrosterone are Not Reflected by Serum Levels of Active Androgens and Estrogens But of Their Metabolites: Intracrinology",*Journal of Clinical Endocrinology and Metabolism*, 82(8):2403-2409 (1997).
Jardinet, et al., "Longitudinal Analysis of Bone Mineral Density in Pre-Menopausal Female Systemic Lupus Erythematosus Patients: Deleterious Role of Glucocorticoid Therapy at the Lumbar Spine", *Rheumatology*, 39:389-392 (2000).
Hughes, et al., "1,25-Dihydroxyvitamin $D_3$ Regulates Estrogen Metabolism in Cultured Keratinocytes", *Endocrinology*, 138(9):3711-3718 (1997).
Harada, et al., "Localized Expression of Aromatase in Human Vascular Tissues", *Circulation Research*, 84:1285-1291 (1999).

(Continued)

*Primary Examiner* — Susan Hanley
(74) *Attorney, Agent, or Firm* — Milbank, Tweed, Hadley & McCloy LLP (57) ABSTRACT

The invention relates to the treatment of wrinkles in the face, wrinkles at open-necked regions, pregnancy strias, and stretched strias on the lower abdomen, thighs or buttocks with a steroidal aromatase inhibitor which also has 5-alpha reductase inhibitor activity which is 4-hydroxyandrostenedione or a derivative thereof.

7 Claims, 3 Drawing Sheets

OTHER PUBLICATIONS

Arnold, S., "Urinary Incontinence in Castrated Bitches. Part 1: Significance, Clinical Aspects and Etiopathogenesis", *Schweiz Arch Tierheilkd*, 139(6):271-276 (1997). (Abstract).

Benson, et al., "Synthesis and Secretion of Transforming Growth Factor Beta Isoforms by Primary Cultures of Human Breast Tumour Fibroblasts in Vitro and Their Modulation by Tamoxifen", *Br. J. Cancer*, 74(3):352-358 (1996). (Abstract).

Berkovitz, et al., "Aromatase Activity in Cultured Human Genital Skin Fibroblasts", *J. Clin. Endocrinol. Metab.*, 59(4):665-671 (1984). (Abstract).

Berkovitz, et al., "Down-Regulation of the Glucocorticoid Receptor by Dexamethasone in Cultured Human Skin Fibroblasts: Implications for the Regulation of Aromatase Activity", *J. Clin. Endocrinol. Metab.*, 66(5):1029-1036 (1988). (Abstract).

Berkovitz, et al., "Testosterone Lowers Aromatase Activity in Cultured Human Genital Skin Fibroblasts", *Mol. Cell Endocrinol.*, 69(2-3):187-197 (1990). (Abstract).

Berkovitz, et al., "Induction and Superinduction of Messenger Ribonucleic Acid Specific for Aromatase Cytochrome P-450 in Cultured Human Skin Fibroblasts", *J. Clin. Endocrinol. Metab.*, 74(3):629-634 (1992). (Abstract).

Bisat, et al., "Influence of Cell Culture Conditions on Aromatase Activity in Human Genital Skin Fibroblasts", *In Vitro Cell Dev. Biol.*, 25(9):806-812 (1989). (Abstract).

Borel, et al., "Hormonal Control of the Metabolism of Collagen", *Pathol. Biol.* (Paris), 32(7):795-812 (1984). (Abstract).

Brenner, S., and Matz, H., "Improvement in Androgenetic Alopecia in 53-76-year-old Men Using Oral Finasteride", *Int. J. Dermatol.*, 38(12):928-930 (1999). (Abstract).

Brodie, A.M., et al., "Lack of Evidence for Aromatase in Human Prostatic Tissues: Effects of 4-Hydroxyandrostenedione and Other Inhibitors on Androgen Metabolism", *Cancer Res.*, 49(23):6551-6555 (1989). (Abstract).

Cassidenti, et al., "Effects of Sex Steroids on Skin 5 Alpha-Reductase Activity in Vitro", *Obstet. Gynecol.*, 78(1):103-107 (1991). (Abstract).

Chen, et al., "Activity of 17beta-(N-Alkyl/Arylformamido) and 17beta-[(N-alkyl/aryl) alkyl/arylamido]-4-Methyl-4-Aza-5alpha-Androstan-3-Ones as 5alpha-Reductase Inhibitors in the Hamster Flank Organ and Ear", *J. Invest. Dermatol.*, 111(2):273-278 (1998). (Abstract).

Chen, et al., "The 5 Alpha-Reductase System and Its Inhibitors. Recent Development and Its Perspective in Treating Androgen-Dependent Skin Disorders", *Dermatology*, 193(3):177-184 (1996). (Abstract).

Chen, et al., "Local and Systemic Reduction by Topical Finasteride or Flutamide of Hamster Flank Organ Size and Enzyme Activity", *J. Invest. Dermatol.*, 105(5):678-682 (1995). (Abstract).

Courchay, et al., "Messenger RNA Expression of Steroidogenesis Enzyme Subtypes in the Human Pilosebaceous Unit", *Skin Pharmacol.*, 9(3):169-176 (1996). (Abstract).

Cummings, et al., "The Effect of Raloxifene on Risk of Breast Cancer in Postmenopausal Women: Results from the MORE Randomized Trial. Multiple Outcomes of Raloxifene Evaluation", *JAMA*, 281(23):2189-2197 (1999). (Abstract).

Davies, et al., "Lipid and Cellular Constituents of Unstable Human Aortic Plaques", *Basic Res. Cardiol.*, 89 Suppl 1:33-39 (1994). (Abstract).

de Loes, et al., "A 7-Year Study on Risks and Costs of Knee Injuries in Male and Female Youth Participants in 12 Sports", *Scand. J. Med. Sci. Sports*, 10(2):90-97 (2000). (Abstract).

Diano. et al., "Aromatase and Estrogen Receptor Immunoreactivity in the Coronary Arteries of Monkeys and Human Subjects", *Menopause*, 6(1):21-28 (1999). (Abstract).

Dijkstra, et al., "Is Increased 5 Alpha-Reductase Activity a Primary Phenomenon in Androgen-Dependent Skin Disorders?", *J. Invest. Dermatol.*, 89(1):87-92 (1987). (Abstract).

Distler, W., "Urinary Incontinence—Taboo During Postmenopause", *Z. Arztl. Fortbild Qualitatssich.*, 94(3):211-215 (2000). (Abstract).

Fujimoto, et al., "Time-Dependent Biphasic Response of Aromatase to Dexamethasone in Cultured Human Skin Fibroblasts", *J. Clin. Endocrinol. Metab.*, 63(2):468-474 (1986). (Abstract).

Gottlieb, et al., "Androgen Insensitivity", *Am. J. Med. Genet.*, 89(4):210-217 (1999). (Abstract).

Gips, et al., "Placental Steroid Metabolism in a Case of Placental Sulfatase Deficiency", *J. Endocrinol. Invest.*, 3(1):51-58 (1980). (Abstract).

Grino, et al., "Testosterone at High Concentrations Interacts with the Human Androgen Receptor Similarly to Dihydrotestosterone", *Endocrinology*, 126(2):1165-1172 (1990). (Abstract).

Hamada, et al., "The Metabolism of Testosterone by Dermal Papilla Cells Cultured from Human Pubic and Axillary Hair Follicles Concurs with Hair Growth in 5 Alpha-Reductase Deficiency", *J. Invest. Dermatol.*, 106(5):1017-1022 (1996). (Abstract).

Harada, N., "A Unique Aromatase (P-450AROM) mRNA Formed by Alternative Use of Tissue-Specific Exons 1 in Human Skin Fibroblasts", *Biochem. Biophys. Res. Commun.*, 189(2):1001-1007 (1992). (Abstract).

Hsiang, et al., "The Influence of 4-Hydroxy-4-Androstene-3,17-Dione on Androgen Metabolism and Action in Cultured Human Foreskin Fibroblasts", *J. Steroid Biochem.*, 26(1):131-135 (1987). (Abstract).

Iida, et al., "Quantitative Comparison of Aromatase Induction by Dexamethasone in Fibroblasts From a Patient With Familial Cortisol Resistance and a Patient With Cortisol Hyperreactive Syndrome", *J. Clin. Endocrinol. Metab.*, 73(1):192-196 (1991). (Abstract).

Itami, et al., "Mechanism of Action of Androgen in Hair Follicles", *J. Dermatol. Sci.*, 7 Suppl:S98-103 (1994). (Abstract).

Jackson, et al., "The Effect of Oestrogen Supplementation on Post-Menopausal Urinary Stress Incontinence: A Double-Blind Placebo-Controlled Trial", *Br. J. Obstet. Gynaecol.*, 106(7):711-718 (1999). (Abstract).

Kwan, et al., "Effects of Sex Hormones on Mesangial Cell Proliferation and Collagen Synthesis", *Kidney Int.*, 50(4):1173-1179 (1996). (Abstract).

Labrie, et al., ""Intracrinology"". Autonomy and Freedom of Peripheral Tissues, *Ann. Endocrinol.* (Paris), 56(1):23-29 (1995). (Abstract).

Labrie, F., "Intracrinology", *Mol. Cell Endocrinol.*, 78(3):C113-118 (1991). (Abstract).

Lachgar, et al., "In Vitro Main Pathways of Steroid Action in Cultured Hair Follicle Cells: Vascular Approach", *J. Investig. Dermatol. Symp. Proc.*, 4(3):290-295 (1999). (Abstract).

Lee, et al. "Decreased Expression of Collagen and Fibronectin Genes in Striae Distensae Tissue", *Clin. Exp. Dermatol.*, 19(4):285-288 (1994). (Abstract).

Leppilahti, J., and Orava, S., "Total Achilles Tendon Rupture. A Review.", *Sports Med.*, 25(2):79-100 (1998). (Abstract).

Lespessailles, et al., "Glucocorticoid-Induced Osteoporosis: Is the Bone Density Decrease the Only Explanation?", *Joint Bone Spine*, 67(2):119-126 (2000). (Abstract).

Libby, et al., "Macrophages and Atherosclerotic Plaque Stability", *Curr. Opin. Lipidol.*, 7(5):330-335 (1996). (Abstract).

Luu-The, et al., "Characterization, Expression, and Immunohistochemical Localization of 5 Alpha-Reductase in Human Skin", *J. Invest. Dermatol.*, 102(2):221-226 (1994). (Abstract).

Mestayer, et al., "Predominant Expression of 5 Alpha-Reductase Type 1 in Pubic Skin From Normal Subjects and Hirsute Patients", *J. Clin. Endocrinol. Metab.*, 81(5):1989-1993 (1996). (Abstract).

Marttunen, et al., "Effects of Tamoxifen and Toremifene on Urinary Excretion of Pyridinoline and Deoxypyridinoline and Bone Density in Postmenopausal Patients with Breast Cancer", *Calcif. Tissue Int.*, 65(5):365-368 (1999). (Abstract).

Milewich, et al., "17 Beta-Hydroxysteroid Oxidoreductases of Human Fetal and Adult Tissues: Immunological Cross-Reactivity with an Anti-Human Placental Cytosolic 17 Beta-Hydroxysteroid Oxidoreductase Antibody", *Placenta*, 11(2):95-108 (1990). (Abstract).

Milewich, et al., "Steroid Metabolism by Epidermal Keratinocytes", *Ann. N Y Acad. Sci.*, 548:66-89 (1988). (Abstract).

Muderris, II., et al., "A Prospective, Randomized Trial Comparing Flutamide (250 mg/d) and Finasteride (5 mg/d) in the Treatment of Hirsutism", *Fertil. Steril.*, 73(5):984-987 (2000). (Abstract).

Nawata, et al., "Aromatase in Bone Cell: Association with Osteoporosis in Postmenopausal Women", *J. Steroid Biochem. Mol. Biol.*, 53(1-6):165-174 (1995). (Abstract).

Oikarinen, et al., "The Molecular Basis of Glucocorticoid-Induced Skin Atrophy: Topical Glucocorticoid Apparently Decreases Both Collagen Synthesis and the Corresponding Collagen mRNA Level in Human Skin In Vivo", *Br. J. Dermatol.*, 139(6):1106-1110 (1998). (Abstract).

Powell, J.W., and Barber-Foss, K.D., "Sex-Related Injury Patterns Among Selected High School Sports", *Am. J. Sports Med.*, 28(3):385-391 (2000). (Abstract).

Rittmaster, et al., "The Effects of N,N-Diethyl-4-Methyl-3-Oxo-4-Aza-5 Alpha-Androstane-17 Beta-Carboxamide, A 5 Alpha-Reductase Inhibitor and Antiandrogen, On the Development of Baldness in the Stumptail Macaque", *J. Clin. Endocrinol. Metab.*, 65(1):188-193 (1987). (Abstract).

Roy, A.K., and Chatterjee, B., "Androgen Action", *Crit. Rev. Eukaryot. Gene Expr.*, 5(2):157-176 (1995). (Abstract).

Sasano, et al., "Aromatase and Sex Steroid Receptors in Human Vena Cava", *Endocr. J.*, 46(2):233-242 (1999). (Abstract).

Sato, et al., "Minoxidil Increases 17 Beta-Hydroxysteroid Dehydrogenase and 5 Alpha-Reductase Activity of Cultured Human Dermal Papilla Cells from Balding Scalp", *J. Dermatol. Sci.*, 19(2):123-125 (1999). (Abstract).

Schwartz, et al., "A Modern View of Atherogenesis", *Am. J. Cardiol.*, 71(6):9B-14B (1993).

Sciore, et al., "Identification of Sex Hormone Receptors in Human and Rabbit Ligaments of the Knee by Reverse Transcription-Polymerase Chain Reaction: Evidence that Receptors are Present in Tissue from Both Male and Female Subjects", *J. Orthop. Res.*, 16(5):604-610 (1998). (Abstract).

Setnikar, et al., "Estradiol and Estrone Plasma Levels During Application of Three Strengths of a 7-Day Estradiol Transdermal Patch", *Arzneimittelforschung*, 49(8):708-715 (1999). (Abstract).

Shozu, M., and Simpson, ER., "Aromatase Expression of Human Osteoblast-Like Cells", *Mol. Cell Endocrinol.*, 139(1-2):117-129 (1998). (Abstract).

Silbiger, et al., "Estradiol Suppresses Type 1 Collagen Synthesis in Mesangial Cells Via Activation of Activator Protein-1", *Kidney Int.*, 55(4):1268-1276 (1999). (Abstract).

Sintov, et al., "New Topical Antiandrogenic Formulations Can Stimulate Hair Growth in Human Bald Scalp Grafter Onto Mice", *Int. J. Pharm.*, 194(1):125-134 (2000). (Abstract).

Svenstrup, et al., "Comparison of the Effect of Cortisol on Aromatase Activity and Androgen Metabolism in Two Human Fibroblast Cell Lines Derived from the Same Individual", *J. Steroid Biochem.*, 35(6):679-687 (1990). (Abstract).

Tamaoka, Y., "A Study on Cellular Interaction Between Theca and Granulosa Cells in Estradiol Biosynthesis by the Human Ovary", *Nippon Sanka Fujinka Gakkai Zasshi*, 39(7):1129-1136 (1987). (Abstract).

Stanczyk, et al., "Androstenedione is an Important Precursor of Dihydrotestosterone in the Genital Skin of Women and is Metabolized Via 5 Alpha-Androstanedione", *J. Steroid Biochem. Mol. Biol.*, 37(1):129-132 (1990). (Abstract).

Thiboutot, et al., "Oxidative Activity of the Type 2 Isozyme of 17Beta-Hydroxysteroid Dehydrogenase (17Beta-HSD) Predominates in Human Sebaceous Glands", *J. Invest. Dermatol.*, 111(3):390-395 (1998). (Abstract).

Theintz, et al., "Developmental Pattern of 17 Beta-Hydroxysteroid Dehydrogenase and 5 Alpha-Reductase Activities in the Foreskin of Boys from Birth to Eight Years of Age", *Horm. Res.*, 32(4):124-129 (1989). (Abstract).

Whiting, et al., "Measuring Reversal of Hair Miniaturization in Androgenetic Alopecia by Follicular Counts in Horizontal Sections of Serial Scalp Biopsies: Results of Finasteride 1 mg Treatment of Men and Postmenopausal Women", *J. Investig. Dermatol. Symp. Proc.*, 4(3):282-284 (1999). (Abstract).

Wojtys, et al., "Association Between the Menstrual Cycle and Anterior Cruciate Ligament Injuries in Female Athletes", *Am. J. Sports Med.*, 26(5):614-619 (1998). (Abstract).

Venencie, et al., "Luteinizing Hormone/Human Chorionic Gonadotrophin Receptors in Various Epidermal Structures", *Br. J. Dermatol.*, 141(3):438-446 (1999). (Abstract).

Winkler, E.M., and Christiansen, K., "Sex Hormone Levels and Body Hair Growth in !Kung San and Kavango Men from Namibia", *Am. J. Phys. Anthropol.*, 92(2):155-164 (1993). (Abstract).

Ye, et al., "Effects of Topical Antiandrogen and 5-Alpha-Reductase Inhibitors on Sebaceous Glands in Male Fuzzy Rats", *Skin Pharmacol.*, 10(5-6):288-297 (1997). (Abstract).

Zhao, et al., "Characterization of the Sequences of the Human CYP19 (Aromatase) Gene That Mediate Regulation by Glucocorticoids in Adipose Stromal Cells and Fetal Hepatocytes", *Mol. Endocrinol.*, 9(3):340-349 (1995). (Abstract).

Mark P. Brincat, "Hormone replacement therapy, and the skin", Maturitas 34 (2000) 107-118.

Office Action dated Jul. 28, 2010; Japanese Patent No. 2001-516551.

Notice of Reasons for Rejection dated Oct. 14, 2011 for Japanese Patent Application No. 2001-516551.

\* cited by examiner

TREATMENT OF WRINKLES AND STRIAS WITH 4-HYDROXYANDROSTENEDIONE OR A DERIVATIVE THEREOF

The present invention relates to the use of substances and agents, which positively influence the peripheric-local, tissue- or organ-cell specific generation of sexual hormones, and to the therapeutic or prophylactic applications related thereto. The present invention particularly relates to the use of such substances and agents for positively influencing collagen. For this purpose, applications for collagen-containing parts of the body are contemplated, such as skin, tendons, fasciae, ligaments, cartilages, bones, dentine, arteries and veins, urinary vessels and other vessel walls. Extremely useful possibilities follow therefrom for the prophylaxis and therapy of various diseases. "Positive influencing" in the terms of the invention means essentially a stabilization, an increase and/or a restoration of collagens or collagen fibres.

As to the background of the invention, the context of the peripheric local, tissue- or organ-cell specific production of sexual hormones will be described in the following.

Testosterone is the essence of the male sexual hormones. Its effects are exhibited via the so-called androgen receptor. Like all steroid hormones, testosterone acts together with its transcriptional factor (Roy 1995), which regulates the transcription. Androgen receptors change their structure upon binding of androgen and move to the cell nucleus towards the corresponding genes, the expressions of which are influenced by androgens. Testosterone itself does not bind particularly strong to the androgen receptor, but first has to be slightly chemically modified within the cell. The enzyme 5-alpha-reductase removes the single double-bond in the steroid hormone molecule, and dihydrotestosterone (DH) is made, which has a tenfold higher affinity to the androgen receptor than testosterone (Grino, 1990). Dihydrotestosterone may also be made from 5-alpha-dihydroandrostendione, which itself was made from androstendione by means of 5-alpha-reductase. This route strongly predominates e.g. in the genital skin of men and women (Stanczyk 1990).

Thus, this conversion, which occurs not before the target organ, i.e. in the periphery, strongly enhances the testosterone-derived effect. For example, in the skin, the effect comprises the promotion of hair growth (except for the scalp) and the increase of the activity of the sebaceous glands. Only cells which have both 5-alpha-reductase-activity and androgen receptors, are allowed to be correspondingly stimulated by testosterone in physiological amounts. The testosterone merely originates from the testicle and, at a minor proportion, also from the adrenal gland. The testosterone level of men is 280 to 1100 nano grams/milli liter and of women 15 to 70 nano grams/milli liters (estradiol: up to 0.45 nano grams/milli liter), resp.

Not only for dihydrotestosterone, but also for testosterone itself, there is an intracellular synthesis route in the periphery (Labrie 1995). Testosterone produced there, however, is not delivered to the blood stream, but acts within the cell where it was made after its conversion into DHT within the same cell. The precursor of the testosterone produced in the periphery is released from the adrenal gland into the blood. The precursor is dehydroepiandrosterone (DHEA), which is present in the blood in micro molar concentrations. Dehydroepiandrosterone is converted into another molecule within the cell, where it has been invaded easily through the cell membrane by simple diffusion. To this end, the 3-beta-hydroxyl group is converted into a keto group, and the double-bond of ring B is transferred into ring A (3-betahydroxysteroid-dehydrogenase/isomerase, 3-beta HSD). Androstendione is produced thereby, from which it is only a little step to testosterone (conversion of the keto group at C-17 into a hydroxyl group by means of 17-betahydroxysteroid-dehydrogenase). This testosterone is then, within the same or other cells, converted into the potent androgen DHT. Using the precursor which is present in the blood at a relatively high concentration, the cells which have the above-mentioned two enzymes therefore can themselves produce, further modify or release testosterone to the environment, where it is contacted with cells which have 5-alpha-reductase and therefore can make DHT.

The extent of conversion of DHEA into androstendione in the peripheral tissue depends from the DHEA level on the one hand, but also from the activity of 3-beta-HSD on the other hand. The latter is probably stimulated by the luteotropic hormone (LH) not only in the testicle, but also in the peripheral tissue (Venencie 1999).

Particular structures in the brain can sensitize testosterone concentrations. When these sensitize them as being too low, a demand is directed to the pituitary gland to the effect that LH is more released. Because of this, the production of androstendione or testosterone in the corresponding peripheral tissue, such as e.g. skin, is also stimulated. If 5-alpha-reductase is present, the androgen effects are then more exerted.

In women, the brain determines the concentration of estrogens instead of that of androgens. A decrease of them also leads, via LH release, to an enhancement of the peripheric conversion of DHEA into androstendione in the correspondingly established tissue. Besides testosterone, androstendione may also be converted into estrone. The enzyme which is responsible therefor is aromatase, which is not as much ubiquitous as the testosterone producing enzyme 17-beta-HSD. Aromatase is also present in the skin (Thiboutot, 1998, Theintz, 1989, Milevich 1988, Sven-strup 1990, Milevich 1990, Dijkstra 1987), but also in other tissue- or organ-specific cells. Estrone is only a weakly effective estrogen and therefore, like testosterone, must be first converted to an active hormone in the target cell in order to fully display its effects. This is done by 17-beta-HSD, which converts estrone in the much more active estradiol. The mechanism of action of estradiol on the cellular level corresponds to that of DHT. It acts via intracellular hormone receptors, which selectively activate as transcription factors the corresponding genes. However, estradiol may also be made intracellularly from androstendione not only via estrone, but also via testosterone, which can also be converted into an estrogen by means of aromatase. This time, it is converted directly into an active estrogen, estradiol. Within a particular target cell, testosterone may also be converted into a highly active androgen or a highly active estrogen by means of a single enzymatic catalytic step, resp., depending on which enzyme is more active. Therefore, in order to provide hormone effects from estrogens or androgens in the peripheral tissue, the organism needs neither ovaries nor testicles, but only an adrenal gland (Labrie 1995, Labrie 1997). Therefore, both men and women can produce in corresponding tissues both estradiol and testosterone. Since the production of highly active hormones and their effects may occur within the same cell, we speak of "intracrinology" (Labrie 1991).

Since aromatase is distributed less ubiquitary than 17-beta-HSD, it is possible that steroids which have to be aromatized have been produced in other cells than estrone or estradiol. Accordingly, the theca cells in the ovary are specialized for the production of androgenic estrogen precursors, and estradiol is produced from them in the adjacent granulosa cells (Tamaoka 1987, Roberts 1990). This is reasonable, because in this case only those cells, the growth of which is connected to the growth of the follicle, release estradiol into the blood, the concentration of which indicates the size of the follicle to the brain. At a specific concentration of estradiol in the blood, ovulation occurs. This is caused by a sudden increase of the concentration of FSH in the blood which is effected by the excess of a specific threshold concentration of estradiol in the blood. The direct production of estrogens from DHEA takes place strongly during pregnancy in the placenta. The essential precursor is the sulfate form, DHEA-S. DHEA-S does not derive from the adrenal gland of the pregnant, but from that of the fetus (Gips 1980). If the delivery or the conversion is ineffective, a diagnostically distinctive decrease of particular degeneration products of estrogens (17-keto-steroids) occur in the urine. If the sulfatase which releases DHEA is missing (inborn ichthyose, which occurs only in boys), there is no increase of the estrogen concentration within the blood of the mother. The extragonadale sexual hormone production in the skin apparently plays a role already within the fetus. A further condition, under which a normal spontaneous birth occurs in spite of hardly present estrogens in the mother blood, is the inborn deficiency of aromatase. The placenta does not convert any more androgens into estrogens, and a moustache even grows in the mother. This may be based on a stimulation of the extragonadale sexual hormone production within the skin of the mother, which results from human choriongonadotropin (hCG). This increased production is apparently responsible for the effect that at those locations, where estradiol is necessary for a normal birth, this production also results from the precursors. The estrogens which are mainly produced by the placenta are biologically quite ineffective. Their increased production is apparently based both on a high concentration of fetal precursors in the funiculus blood and on the stimulus of aromatase by means of the pregnancy-hormone hCG, the beta-chain of which is almost identical with that of FSH and therefore also displays identical biological effects. In the pregnant woman, the peripheral production of sexual steroids is also enhanced in the organs which have LH/hCG-receptors (or possibly receptors for another messenger agent). Certainly, the skin belongs to such organs (Venencie 1999, You 2000).

The object of the invention is to favourably influence the extragonadal sexual hormone production in order that therapeutic effects are enabled through the peripheric-local, tissue- or organ-cell specific presence or absence of sexual hormones.

According to the present invention, it was surprisingly found that collagen can be positively influenced in the collagen-containing body parts concerned by using a substance which is capable of inhibiting the production and/or the effect of estrogens. After the application of the substance or a composition containing this substance, the collagen is stabilized, increased and/or restorated in the collagen-containing body parts.

With this concept, the present invention follows a fundamentally new approach. The central issue of this concept is a targeted intervention in the peripheric-local, tissue- or organ-cell specific production of sexual hormones by means of substances which are particularly suitable therefor, that is essentially those substances which inhibit the production and/or the effect of estrogens. Since aromatase was found to be a key enzyme in this context, aromatase inhibitors serve as particularly suitable substances of the invention for being used according to the present invention. The concurrent or additional inhibition of the production of dihydrotestosterone may also be preferably effective, particularly when applied to the skin. To this end, preferably 5-alpha-reductase inhibitors, but also alpha-receptor blockers are contemplated.

It was surprisingly found that said substance(s) or the composition containing this (these) substance(s) exhibit as a consequence of their action a positive influence on the collagen, particularly on the content of the collagen fibres within the collagen containing body region such as the skin, thereby rendering these body region more tight or firm. By means of biopsies it was found that the proportion of collagen fibres increased. It is considered that—in fundamental contrast to the natural influence via the estrogen level in the blood as well as in contrast to the known estrogen replacement therapy (HRT)—a positive influence on the collagen can be achieved at the specific target location when the local extragonadal estrogen production and/or the local effect of estrogens is reduced or inhibited by using the specific substance or the composition containing this substance according to the use of the present invention.

In a further aspect of the invention it was found that negative influencing factors, which may disadvantageously affect the content and stability of collagens, can be compensated at least partially by using the substance or the composition containing this substance, and harmful effects on the human body can be ameliorated thereby. As such negative influencing factors, there were identified particularly the increased release of LH, the production of vitamin D as a result of an exposure to sun illumination, and the excessive presence or the administration of glucocorticoids.

As a result of the concept of the invention as mentioned above, significant implications and useful cosmetic and therapeutic uses are provided which are exemplified in further detail below. For the medical applications, the suitable substances can be used, together with the pharmaceutically acceptable additives which are typical for the respective mode of application, for the production of an agent or a pharmaceutical formulation and can be applied in the therapeutic uses.

The term "estrogens" shall be construed to mean all natural, female sexual hormones which have estrogen-like effects, such as estradiol, estrone and estrol.

As substances which are inhibitory in terms of production and/or effect of estrogens, particularly two classes of substances which will be described in further detail in the following are contemplated.

On the one hand, these are anti-estrogens, i.e. substances which block estrogen receptors and therefore inhibit the effect of estrogen as antagonists.

Furthermore, these are substances which may inhibit the ex-=tragonadal production of estrogens locally. To this end, steroidal and non-steroidal inhibitors of the (cytochrome-p450)-aromatase are contemplated. Aromatase is the central enzyme which catalyses the chemical conversion of the precursor molecules (such as dehydroepiandrosterone (DHEA) and androstendione), which derive from the adrenal gland and are trans-ported via the blood, into estrogens. As a consequence, the inhibition of this enzyme leads to a local in situ inhibition of the estrogen production. Because of their particularly beneficial course of action, the aromatase inhibitors are preferred for the application of the use according to the present invention.

Examples of aromatase inhibitors include the following substances:

Steroidal aromatase inhibitors:
4-hydroxyandrost-4-ene-3,17-dione (Formestan and Lentaron),
6-methylene-androstra-1,4-diene-3,17-dione (Exemestan),
10-(2-propynyl)estr-4-ene-3,17-dione (MDL 18962)
7-alpha substituted androstendionee-derivatives
1,4,6-androstatriene-3,17-dione (ATD)
10-oxirane- and 10-thiirane substituted androgens
10-propargylestr-4-ene-3,17-dione
10-propargylestr-4-ene-3,17-propionate 10-(2-propynyl)-derivative
13-retro-antiprogestine
14-alpha-hydroxy-4-androstene-3,6,17-trione (14 alpha-OHAT)
16- or 19-substituted androst-4-ene
19-(cyclopropylamino)-androst-4-ene-3,17-dione
19-(ethyldithio)-androst-4-ene-3,17-dione (ORG 30958)
19-oxiranyl- and 19-thiiranyl-steroids
19-thiomethyl- and 19-azido-androstenedione
1-methyl-androsta-1,4-diene-3,17-dione (Atamestan)
2,2-dimethyl-4-hydroxy-4-androstene-3,17-dione
3-alpha-methoxyandrost-4-ene-6,17-dione
3-beta-hydroxyandrost-4-ene-6-one-derivatives
3-deoxyandrogen-19-oxygenated derivatives of 3-oxo-17-beta-carboxamido steroids
4-(phenylthio)-4-androstene-3,17-dione
4-(thio-substituted)-4-androstene-3,17-dione
4-acetoxy-4-androstene-3,17-dione
4-amino-androstenedione
4-androstene-3,6,17-trione
4-hydroxyandrostenedione (4-OHA, CGP 32349)
4-methoxy-4-androstene-3,17-dione
4-oxygenated androst-5-en-17-one and their 7-oxo-derivatives
4-thiosubstituted derivatives of 4-androstene-3,17-dione
4-thiosubstituted-4-androstene-3,17-dion-derivatives
5-alpha-dihydro-norethindrone (a metabolite of norethindrone)
5-alpha-reduced C19-steroids
5-alpha-androstane-17-ones with or without a carbonyl functionality at C-3 and/or C-6
6-alpha,7-alpha-cyclopropane derivatives of androst-4-ene
6-alpha-fluorotestosterone
6-beta-propynyl substituted steroids
6,7-aziridinyl steroid und related compounds
6-alkyl analogs of delta-1,4,6-androgens
6-alkyl analogs of delta 4,6-androgens
6-alkyl- and 6-arylandrost-4-ene-3,17-dione
6-alkylandrost-4-ene-3,17-dione of 7-alpha- and 7-beta-arylalkyl-substituted androst-4-ene-3,17-diones
6-alkylandrosta-4,6-dien-3,17-dione und their 1,4,6-triene-analogs
6-alkyl-substituted androgens
6-phenylalkyl-substituted C19-Steroids with 1,4-diene-, 4,6-diene- or 1,4,6-triene-structure
6-bromoandrostenedione
6-hydroxy-iminoandrostenedione
6-methylenandrosta-1,4-diene-3,17-dione (FCE 24304)
6-phenylalkyl-substituted androst-4-ene-3,17-dione
6-substituted androst-4-ene-analogs
7-alpha-(4'-amino)phenylthio-4-androstene-3,17-dione
7-alpha-substituted androsta-1,4-diene-3,17-dione
7-alpha-substituted androstenedione
7-alpha-(4'-amino)phenylthio-4-androstene-3,17-dione
7-alpha-arylalkylated androsta-1,4-diene-3,17-dione
7-alpha-substituted androstenediones
7-substituted 4,6-androstadiene-3,17-dione
7-substituted steroids
androst-4-ene-3,6-dione derivatives
androst-5-ene-7,17-dione-19-nor- and 5-beta,6-beta-epoxy-derivatives
A- or B-ring-substituted derivatives of androst-4-ene-3,6,17-trione
A-ring linked steroids
bromoacetoxy-4-androstene-3-one
delta-1,4,6-androgens
delta-4,6-androgens
epimeric 6-hydroperoxyandrostendionees
estr-4-ene-3,17-dione (MDL 18 962),
estr-4-ene-3,6,17-trione
flavonoids
RU486

Non-steroidal aromatase inhibitors:
6-[(4-chlorophenyl)(1H-1,2,4-triazole-1-yl)-methyl]-1-methyl-1H-benzotriazole (Vorazol),
2,2'-[5-(1H-1,2,4-triazole-1-yl-methyl)-1,3-phenylene]bis(2-methylproprionitrile) (Arimidex),
4-[1-(cyanophenyl)-1-(1,2,4-triazolyl)methyl]benzonitrile (Letrozol),
{4-(5,6,7,8-tetrahydro-imidazo-[1,5a]-pyridine-5-yl)-benzonitrile monohydrochloride (Fadrozol)
pyridoglutethimide (Rogletimid).
aminogluthethimide
1,2-imidazolyl-methyl-cyclopentanol-derivatives
1-[(benzofurane-2-yl)phenylmethyl]-triazole and -tetrazole
1-[benzofuran-2-yl)-phenylmethyl]-imidazole (substituted)
1-(benzofurane-2-ylmethyl)imidazole of N,N-disubstituted-5-aminopyrimidine-derivatives
1-imidazolyl(alkyl)-substituted di- and tetrahydroquinoline
1-pentyl-3-(4-aminophenyl)pyrrolidine-2,5-dione
1-phenyl-3-azabicyclo[3.1.0]hexane-2,4-dione
1-phenyl-3-azabicyclo[3.1.0]hexane-2,4-dione and analogs
3-alkylated 3-(4-aminophenyl)piperidine-2,6-dione
3-cycloalkyl-substituted 3-(4-aAminophenyl)piperidine-2,6-dione
3-ethyl-3-(4-pyridyl)piperidine-2,6- and 5-alkylderivatives
3-ethyl-3-(4-pyridyl)piperidine-2,6-dione-analogs
4-amino-4H-1,2,4-triazole-derivatives
4-cyclohexylaniline
aminoglutethimid
benzimidazole- and imidazole-compounds
delta-1,4-bis-norcholadienic acid
delta-1-testolactone
imidazole derivatives of pyrrolidonic and piperidonic
imidazolyl-1,3,5-triazines
MR 20492 and MR 20494 (two indolizinone derivatives)
pyridyl-substituted indanone, indane and tetralines
s-triazine derivate SEF19
substituted pyridines
testololactone Other aromatase inhibitors:
8-bromo-cyclic adenosine mono-phosphate
FR901537
hexamethyl melamine derivative (SAE9)
insulin sensitizers troglitazone and ketoconazole
Letrozole (CGS 20267)
Mefloquin
MPV-2213ad
N-n-octanoyl-nornicotine and other nor-nicotine derivatives
Org 33201
R 76713 and R 76713
sesqui-terpene lactones SH 489
TAN-931
thyroid hormones
tobak alkaloid derivatives
YM511

As to the specifications of these substances as well as their availability, it is referred, for example, to "Rote Liste", Editio Cantor, Aulendorf (DE) (1999).

Such aromatase inhibitors are known as such, mainly as systemically applied therapeutic agents for the medical therapeutic treatment of breast cancer. In this connection, it is referred to the review article of A. M. H. Brodi in: "J. Steorid Biochem. Molec. Biol.", Vol. 49, No. 4-6, pp. 281-287 (1994), P. E. Goss and K. M. E. H. Gwyn in. "Journal of Clinical Oncology", Vol. 12, No. 11, pp. 2460-2470 (1994). For the determination of the aromatase inhibition and the subsequent decrease of estrogens, it is referred to the further literature citations which are indicated in the mentioned review articles, see for example A. M. H. Brodi et al. in: "J. Steroid Biochem. Molec. Biol.", Vol. 7, pp. 787-793 (1976), and D. A. Marsh et al. in: "J. Med. Chem.", Vol. 28, pp. 788-795 (1985).

Specific azole derivatives and their aromatase inhibiting and anti-mycotic effect are further described in EP-A-0 575 210.

It was found that substances having aromatase inhibiting properties are contained in soya glycines (INCI name according to the Linné-system), and that these soya glycine derived aromatase inhibitors can be used according to the present invention. These soya glycine derived aromatase inhibitors can be readily obtained by providing "glycine soya" (soy bean oil or soy bean extract, or soya sterole), and subsequently isolating the component having aromatase inhibiting effects by means of typical separation methods, such as liquid chromatography, particularly by means of HPLC.

It was further found that the aromatase inhibiting effect of soya glycine may be enhanced, when the soya glycine is treated by oxidation. The synthesis of this oxidized form derived from soya glycines is readily carried out by means of oxidation of soya glycine (soy bean oil or soy bean extract, or soya sterol), and the subsequent isolation of the component with aromatase inhibiting effect by means of typical separation methods, such as liquid chromatography, particularly by means of HPLC. The oxidation can be carried out by an enzymatic approach, for example according to the method described by Y. Fujimoto et al. in: "J. Am. Chem. Soc.", Vol. 104, pp. 4718-4720 (1982), or by a chemical approach, for example according to the method described by P. Wetzel in: "Tetrahedron", Vol. 41, No. 20, pp. 4509-4517 (1985).

As examples for substances of the class of anti estrogens, there are mentioned particularly the non-steroidal estrogen antagonists Tamoxifen (Z-2-[4-(1,2-diphenyl-1-butenyl)-phenoxy]-N,N-dimethylamine) and aminoglutethimide (3-(4-aminophenyl)-3-ethyl-2,6-piperidin-dione) as well as their analogs and derivatives, for example 3-hydroxytamoxifen, 4-hydroxytamoxifen and 7-α-alkyl-sulfinyl-tamoxifen-analogs (ICI 182,780).

Concerning the specifications of these substances, their availability as well as further suitable anti estrogens, see, for example, "Rote Liste", Edition Cantor, Aulendorf (DE) (1999).

Likewise, these anti estrogens have been hitherto described mainly in connection with the systemic therapeutic treatment of breast cancer.

In order that the extragonadal, cellular production or effect of sexual hormones can be enabled more specific and be better adjusted, one or more of the substances described above for the inhibition of the production and/or the effect of estrogens may be combined with a further effect principle such that the production and/or the effect of dihydrotestosterone is inhibited additionally or concurrently. This is effected by the use of a 5-alpha-reductase inhibitor or an alpha-receptor blocker, wherein the use of a 5-alpha-reductase inhibitor is particularly preferred.

Examples of 5-alpha-reductase inhibitors, distinguished according to the respective type, include:
Type 1 inhibitors:
LY191704 (benzochinolinone)
4,7-beta-dimethyl-4-azacholestane-3-one (MK-386) and related 4-azasteroids
benzo[c]chinolizine-3-one
Type 2 inhibitors:
benzophenone- and indole carboxylic acids
N-tert-butyl-3-oxo-4-aza-5α-androst-1-ene-17-β-carboxamide (Finasterid)
Dual inhibitors (Type 1 and Type 2):
3-carboxy-20-keto-steroids
6-azasteroid
4-aza-3-oxo-5-alpha-androst-1-ene-17-beta-N-aryl-6-azasteroids
FK143
Non-steroidal inhibitors:
4-(1-benzoyl indole-3-yl)butyric acid
4-[3-[3-[bis(4-isobutylphenyl)methylamino]benzoyl]-1H-indole-1-yl]-butyric acid
benzanilide-derivates
carbamoylalkenyl-phenyloxy carboxylic acid derivates
ethyl-4-(1-methyl-2-oxopiperid-5-yl)benzoate
FK143
N,N-bis(1-methylethyl)-4-[3-(1,2-dihydro-1-methyl-2-oxopyrid-5-yl)propyl]benzamide
phenoxybenzoic acid derivatives
carboxamide- and phenylalkyl-substituted pyridones and piperidones
natrium-4-[2-(2,3-dimethyl-4-[1-(4-isobutylphenylethoxy]benzolamino)phenoxy]butyrate (ONO-3805)
(Z)-4-2-[[3-[1-(4,4'-difluorobenzhydryl)indole-5-yl]-2-pentenoyl]-amino]phenoxy]butyric acid (KF20405)
Steroidal inhibitors:
17-beta-(N,N-diisopropylcarbamoyl)estra-1,3,5(10)-triene-3-sulfonic acid
17-beta-carbamoyl-1,3,5(10)-estratriene-3-carboxylic acid
17-beta-N,N-diethylcarbamoyl-4-methyl-4-aza-5-alpha-androstan-3-one (4-MA)
17-beta-N-(2-methyl-2-propyl)-carbamoyl-androst-3,5-diene-3-carboxylic acid
3-androstene-3-carboxylic acid (steroidal acrylates),
3-carboxy-17-beta-substituted steroid
4-aza-3-oxo-steroid family
4-hydroxy-androstenedione
4-methyl-4-aza-5-alpha-pregnan-3-one-20(S)-carboxylate
6-methylene-progesterone-, -androstene- and -androstane derivatives
Finasterid
progesteron
natrium-4-methyl-3-oxo-4-aza-5-alpha-pregnane-20(S)-carboxylate steroidal A-ring arylcarboxylic acids
TZP-4238 (steroidal antiandrogen)

As an example for an alpha-receptor blocker, R-(−)-5-{2-[2-(2-ethoxyphenoxy)ethylamino]peropyl]-2-methoxy-benzolsulfonamid (Tamsulosin) may be mentioned.

These substances for the inhibition of the production and/or effect of dihydrotestosterone are also known as such, but only for the treatment of benign prostate hyperplasy (see "Rote Liste", Editio Cantor, Aulendorf (DE), (1999)).

As particularly suitable substances, those are contemplated which exhibit both an inhibitory effect on aromatase and on 5-alpha-reductase. As examples for substances having this bifunctional property, there can be mentioned the sterol 4-hydroxy-androstendionee, which is similar to androstenedione, and its derivatives, e.g. Formestan mentioned above, or the soya sterols.

Since, according to the present invention, the concurrent inhibition of the production or effect of both estrogens and dihydrotestosterone was found to be novel and significant predominantly for topical applications to the skin and for controlling hair growth, as will be described in further detail below, the present invention further provides a topic composition, i.e. a composition which is determined to be applied to the skin, which composition comprises one or more substance (s) such that the production and/or the effect on estrogens and, at the same time, the production and/or the effect of dihydrotestosterone are inhibited. Such a composition is particularly cosmetically applicable in a topical formulation to be applied locally. This combined effect principle may be obtained by a combination of substances which have the property of inhibiting the production or effect of estrogens, on the one hand, and the property of inhibiting the production or effect of dihydrotestosterone, on the other hand, respectively, wherein the substances having the respective functions mentioned above are suitable. Because of an improved controllability, a combination of an aromatase inhibitor with a 5-alpha-reductase inhibitor is preferred in this context. To this end, an embodiment is particularly preferred, wherein an applied substance is bifunctional as explained above and has properties of aromatase inhibition and 5-alpha-reductase inhibition.

The substance or the substances described above can be administered in typical pharmaceutical formulations. Accordingly, as desired and as selected, the pharmaceutical formulations contain the typical and known additives for an oral or a topical application, for injections, for inhalations or for transdermal therapy, respectively. A pharmaceutical formulation is preferably designed to be suitable for a topical application or for a transdermal therapy, for injection or for inhalation.

The content of the therapeutically effective substance for the inhibition of the production or effect of estrogens in such formulations is not problematic and may be adjusted according to the respective treatment case. For example, a content of therapeutic substance in the total composition is suitable from 0.0001 to 10 percent by weight (wt. %), preferably 0.001 to 5 wt. % and particularly 0.3 to 2 wt. %. The further, optionally present additives may be used in amounts which are typical for the respective formulations. Corresponding considerations are valid for the optional additional use of the therapeutic substance for the inhibition of the production or effect of dihydrotestosterone.

If the different effect mechanisms for the control of production or effect of estrogens and, optionally, the production or effect of dihydrotestosterone shall mutually supplement and favourably influence each other, the substances suitable therefor, which have been described above, are used in a balanced proportion in order to achieve a desired effect. The content proportion which is to be applied in this combination may be adjusted to the respective demands. Accordingly, either the substance of one type or the substance of the other type may for example predominate, depending on which mode of action is primarily desired. The weight proportion of the amounts of the one to the other type of substance, for example, lies in a range of 90/10 to 10/90, particularly in a range of 60/40 to 40/60.

Various aspects of the present invention are based on particular conditions in the human body, which exhibit one or more of the following criteria:
- increased activity of aromatase,
- increased expression or production of LH and/or hCG in the human body,
- increased expression or production of glucocorticoids in the human body, or the therapeutic administration of glucocorticoids, and
- increased production of vitamin D, for example as a consequence of exposure to the sun.

These conditions may be present spontaneously or permanently, or in addition inherently by means of natural or pathologic circumstances, or may occur by means of external effects. The potential stimulation of the enzymes which are involved in the extragonadal sexual hormone production, including aromatase and possibly also 5-alpha-reductase, may be seen as the common basis for these influencing criteria. However, the use of the substances mentioned above according to the present invention counteracts a decrease or weakening of collagen as a cause of this stimulation. Among the organs or tissues which contain aromatase, there are skin, connective tissue, bones, vessel walls (even the vena cava contains in its wall aromatase [Sasano 1999]), blood cells (particularly macrophages), muscles, uterus, brain and others.

Therefore, taking account of the mentioned criteria, profiles of therapeutic uses having a high priority are brought about which have great importance due to the high prevalence of the underlying diseases, such as osteoporosis, varicose veins and ulcus cruris, arteriosclerosis, myocardial infarction and urinary incontinence. In this connection, the skin, tendons, bones and the walls of vessels and of downstream urinary passages are of particular importance due to their collagen contents.

Likewise, particular groups of persons may be especially affected, e.g. postmenopausal women.

The cause for this is eventually not ascertained, but the following may be assumed: the activity of the enzymes, which are involved in the extragonadal production of sexual hormones, is allowed to be stimulated by LH or hCG. Naturally, aromatase belongs to this group of enzymes. The extragonadal production of sexual hormones is allowed to be stimulated not only by an enhancement of the involved enzymes via LH, but also through the provision of higher amounts of precursors. LH-receptors are present in the adrenal gland. These are located on steroido-genic cells, which produce DHEA (Pabon 1996). The activity of aromatase is further allowed to be stimulated specifically by means of glucocorticoids (Harada 1992), which enhance the transcription of the m-RNA of aromatase. In the cells of the skin, the stroma cells of the fatty tissues and in osteoblasts, the promoter of exon 1, which is expressed in a tissue specific manner, has a glucocorticoid-responsive element, to which the glucocorticoid receptor binds and enhances the transcription of the aromatase gene (Zhao 1995). The postmenopausal phase is a condition with a permanently increased concentration of LH and its releasing hormone LHRH or GnRH, which controls the release of LH from the hypophysis. Permanently increased LH concentration should lead to a permanently increased local production of estradiol in tissues which may react hereto and have aromatase. This would result in a decrease of their contents of collagen fibers.

In the following, individual examples will be described for particularly suitable application fields and methods of treatment.

Skin

An essential change of the skin during pregnancy are pregnancy strias which are interpreted as stretched strias or streaks. Similar strias are likewise found in Morbus Cushing, which is a condition associated with permanently increased blood levels of glucocorticoids caused by the replacement of cyclic variations of blood ACTH levels by an even level of the ACTH concentration. A characteristic of the skin of pregnancy strias is a decrease of collagen content. The gene for type I and type II collagen are expressed only at 10% compared to normal skin (Lee 1994). Aromatase is present in the skin both in fibroblasts and in keratinozytes (Berkowitz 1984, Fujimoto 1986, Bisat 1989, Harada 1992, Hughes 1997, Lachgar 1999). In both cells, their expression can be enhanced by glucocorticoids (Harada 1992, Berkowitz 1992, Ida 1991, Svenstrup 1990, Berkowitz 1981, Hughes 1997). Accordingly, a review article of the year 1984 concludes that glucocorticoids, but also estradiol have collagen decreasing effects (Borel 1984). Recently, the collagen decreasing effect of estradiols on the molecular level could be shown directly in the mesangium cells of renal glomerula (Neugarten 1999, Silbiger 1999, Kwan 1996).

The established scholarship opinion, however, is that the skin is an estrogen dependent organ, wherein estrogen should not lead to a decrease, but to an increase of collagen fibres within the skin.

Collagen of the skin essentially is of type I. Accordingly, M. L. Barklink et al. ("J. Appl. Physiol." 1993, 74(2), p. 727-732) have found that the bone mass and the collagen content of the skin decrease with increasing age. It was found that a correlation exists between a decreased content of collagen within the skin and the decreased estrogen level in the blood which is associated in the menopausal phase with increasing age. D. Gruber et al ("Klin. Wochenschrift" (Wien) 1995, 107, p. 622-625) report that the estrogen dependent, postmenopausal decrease of the collagen tissue can be assessed by means of sonography, and they assume that a successful therapy is possible by the optimization of a dose for an estrogen replacement therapy (hormone replacement therapy, HRT). Other experts (see e.g. "Therapie" 1996, 51, p. 67-70, and "Dermatology" 1996, 193, p. 289-294) also try to respond to the skin aging which occurs particularly in the postmenopausal phase.

However, it was not confirmed that estrogens may increase the collagen content of the skin. Accordingly, implants of estradiol lead to a significant reduction of the immature "crosslinks" hydroxylsinorleucine (Holland 1994). The percentage of collagen content and the proportion of major "crosslinks" (histidino-hydroxylsinorleucine) of the skin do not change.

The HRT (hormone replacement therapy) neither changes the amount nor the synthesis ratio of collagens in the skin (Haapasaari 1997). It is found occasionally that the relative proportion of collagen type III shall increase after administration of estrogen (Savvas 1993, Schmidt 1996).

When treating collagen deficiency conditions of the outer skin, such as e.g. anatony or slackness of outer skin, the formation of wrinkles and stretched strias, it was found according to the present invention that the positive influence on the collagen is effected locally in the cutis, that is in epidermis and corium. Thus, contrary to the official scholarship opinion, but being founded by experimental studies, the finding is established that estradiol has a direct local collagen decreasing effect, while it is realized according to the present invention that the content of collagen fibres of the skin is increased by means of a local inhibition of aromatase activity within the skin by using the substances described above or by corresponding measures for locally inhibiting the production or effect of estrogens.

The topic inhibition of aromatase within the skin may be utilized to increase the percentage of collagen fibres of the skin locally. This is of importance when cosmetically treating wrinkles in the face and at open-necked regions or when cosmetically influencing pregnancy strias or stretched strias at the lower abdomen, the thighs and the buttock (which is well visible especially in the case of dark skin color).

A part of the substances and their ability for treating disordered connective fatty tissue of the inner skin, such as cellulite, or their use for smoothening and/or reducing fat cell containing body regions are already known from WO-A-97/36570 and WO-A-99/17712. However, the phenomena described there occur in the inner skin fatty connective tissue of the subcutis, whereas this skin aspect of the present invention is directed to the part of the skin which particularly contains collagen, that is the cutis (epidermis and corium) as well as other parts of the body which strongly contains collagen. In particular, no hints are to be found in these references on the surprisingly found correlation between the inhibition of the production, on the one-hand, and the effect, on the other hand, of local estrogens and a positive, direct influence on the collagen locally in the cutis, which is both anatomically and functionally different from the subcutis.

Consequently, a complete functional penetration of the skin down to the subcutis is not necessary according to the present invention in order to display the described effects in the cutis itself. The positive influence of the collagen according to the present invention is effected via the relative deficiency of estrogens directly in the epidermis and in the corium of the cutis. This is because the cutis of the skin is capable of forming estrogens from androgens (Bulun 1998), because both fibroblasts (Macdiamid 1994, Toda 1994, Staib 1994, Jakob 1995, Isurugi 1996) and kerationzytes (Hughes 1997) have the aromatase enzyme. Furthermore, epidermis and corium are estrogen-dependent skin layers and, therefore, must also have estrogen receptors (Hughes 1997 on keratinozytes, Dieudonne 1998 on fibroblasts). Since the aromatase activity of the skin (particularly of the female skin) is expressed constitutionally and estrogens decrease the content of collagen fibres, the female skin constitutionally does not contain as much collagen fibres as the male skin, which is also much thicker. Upon a decrease of the local estrogen concentration in the female skin, the collagen fibres are increased. Since the estrogen concentration of the female skin is predominantly effected by means of the local activity of aromatase, a decrease of the local estrogen concentration is achieved by means of an inhibition of the aromatase activity in the keratinozytes and the skin fibroblasts. Therefore, the inhibition of the skin aromatase leads to an increase of collagen fibres, especially those of type I, and accordingly to an increase of the thickness and the tightness of the skin. These phenomena are noticed by the female probands tested within the framework of the invention and were experimentally demonstrated after about 4 weeks treatment duration.

The topical inhibition of aromatase in the skin results in that only the route to testosterone is open for androstendione. Testosterone itself also cannot be aromatized to estradiol, but is converted into the strong androgen DHT when 5-alpha-reductase is active. The skin is rich in 4-alpha-reductase (Mestayer 1996, Courchay, Luu-The 1994) and thereby can exhibit the typical male appearance (Bart, sebaceous glands, thickness). Estradiol is capable of inhibiting 5-alpha-reductase (Cassidenti 1991). Now, if aromatase is inhibited, there is a depletion of estradiol of the skin. The inhibition and the estradiol deficiency are two factors which provide a remarkable predominance to 5-alpha-reductase. Therefore, it is possible that if only aromatase is topically inhibiting, some virilization of the skin may occur. Additionally, testosterone already provides a half maximum inhibition of aromatase in small amounts (6 nano mole/L) (Berkovitz 1990). By inhibiting 5-alpha-reductase, an enrichment of the skin with testosterone and therefore also an inhibition of the aromatase are achieved.

It is desired that a virilization is avoided particularly in the face. Therefore, it is very advantageous that 5-alpha-reductase is inhibited together with the aromatase, if the collagen content of the skin is desired to be increased locally. A lack of inhibiting 5-alpha-reductase apparently would enable an even further increase of the collagen content of the skin, but with the expense of virilization. Since a local collagen increase is produced in the skin when inhibiting both enzymes, the estrogen depletion alone appears to be sufficient therefor. An accompanying inhibition of both the aromatase and the 5-alpha-reductase may occur either with corresponding soya steroles or with known drug substances (Hsiang 1987, Brodie 1989, Brodie 1989). Both the aromatase and the 5-alpha-reductase act at the 3=4-double bond in ring A of the sterole core structure. It is described in the literature that 4-hydroxyandrostendione in higher concentrations (3 micro mole/L) can also inhibit 5-alpha-reductase. The critical concentration for aromatase lies at about 3 nano mole/L. Therefore, e.g. soya steroles which inhibit aromatase also exhibit an inhibiting effect on 5-alpha-reductase.

For positively influencing collagen in the cutis of the skin, a formulation suitable for the usable substance to be applied for the topical administration of the described therapeutic substance(s) or the composition may be selected, e.g. an ointment, a cream, a gel, an emulsion (lotio), a powder, an oil, etc. For this purpose, the composition comprises additives which are typical for the corresponding formulations as ointment, cream, gel, emulsion, powder or oil, etc. Known as well as commercially available, conventional skin care agents are well suitable in the respective formulations for use in the present invention. As typical additives for such formulations, there are, for example, plant oils such as almond oil, olive oil, peach-stone oil, peanut oil, castor oil and the like, plant extracts, etheric oils, vitamin oils, fatty and fat-like substances, lipoids, phosphatides, hydrocarbons such as paraffins, vaseline, lanoline, waxes and the like, detergents, further skin agents such as lecithine, lanoline, alcohols, carotin and the like, skin nutritions, perfumes, cosmetic agents, alcohols, glycerol, glycols, urea, talcum, conservation agents, sun protection agents, dyes such as titan white and zinc white, antioxidants, etc. Generally, water serves as the basic substance, thereby usually producing, with the addition of emulsifiers such as fatty alcohol sulfate, alkali soaps, lecithine, tri-ethanolamine and the like, an O/W- or W/O emulsion.

Other Collagen Containing Body Regions

Based on the surprisingly found possibility of stabilizing, increasing and/or restorating collagen in the cutis of the skin by means of the specific substances, the invention is applicable not only there, but also to other, particularly collagen-containing parts of the body in terms of local target areas of application, such as cartilages, tendons, ligaments, fasciae, vessel walls of arteries and veins, such as varicose veins, or of urinary passageways, collagen-containing ulcii such as ulcus cruris, dentine, bones, the collagen capsules of arteriosclerotic plaques, and the like.

The rupture of the anterior sacrum of the knee is a typical injure of sportive women which affect the binding tissue. This occurs much more often in women then in men (Powell 2000, de Loes 2000). This is particularly true for the time of ovulation (Wojtys 2000). Then, the highest LH level in the blood is also found and therefore the highest extragonadal formation of sexual steroids in women in the premenopausal phase. Apparently, a somewhat higher local estrogen concentration within the ligament makes it more susceptible to injuries. The ligaments of the joint of the knee have estrogen receptors (Sciore 1998).

Accordingly, the substance or the composition containing this substance may optionally be used in support of surgical operations of such body parts having high collagen contents. The use for cosmetic purposes is preferred, also within the framework of cosmetic surgery. However, the substance or composition to be used according to the present invention is also suitable as an alternative to surgical measures, for example to support or produce cartilage mass, or to strengthen tendons and ligaments. A further beneficial field of application therefore is sports medicine, where aberrations or even injuries of tendons, ligaments, muscles and cartilages caused by sport stresses are the subject of counteractions.

For such applications, in particular topical formulations as those which have been described above in connection with the skin applications, or injections of physiologically acceptable liquids or suspensions, which contain one or more of the described substances, in or at the desired target location are particularly suitable. Concerning the injections, the kind of carrier liquid and the other components are determined according to the respective place of application and are well-known to the person skilled in the art.

Osteoporosis

During the menopausal phase, there is a continuous chronic lost of bone substance. Since the supportive proteins of the bone decrease continuously, the bone suffers from binding less calcium phosphate. This results in a decrease of bone density which can be determined by X-ray methods. This development could be retarded conventionally by the administration of estrogens or of estrogens and gestagens (hormone replacement therapy; HRT). The administration of androgens also has a beneficial effect. The mechanism of protecting bones by means of very low concentrations of estrogens or androgens in the blood, which are, besides, present there by being bound to carrier proteins, is not known.

Since osteoblasts contain aromatase (Shozu 1998, Tanaka 1996), the considerations explained above allowed to expect that the decrease of bone mass is based on the collagen decreasing effect of the increased local production of estrogens. The stimulus of this, i.e. the postmenopausally increased concentration of LH, would be remarkably lowered by the administration of hormones, and the resorption by the bones would therefore be diminished—which explains the effect of the conventional HRT. In fact, the aromatase activity in the bones correlates with the extent of osteoporosis (Nawata 195).

Following the new concept of the present invention, it is now possible to stop the continuation of osteoporosis by means of inhibiting aromatase. Optionally the aromatase inhibition can be carried out topically, by means of diffusing the steroidal hydrophobic drug through the skin, by a transdermal system or by an inhibitor introduced into the blood systemically, by means of injecting a depot of a drug in the muscular system, or by inhalating the drug. For topical applications, the 4-hydroxy-androstendione, which is market-approved (trade name: Lentaron), is particularly suitable. As a sterol being almost identical to androstendione, it easily permeates the skin and occupies upon contact with aromatase irreversibly in the active center thereof (suicide inhibition). An oral administration is therefore obsolete.

The effect of estrogens may also be realized by means of blocking the estrogen receptors via the anti-estrogens mentioned above. Tamoxifen, which is applied in the hormone therapy of breast cancer, is offered here as the most widespread substance.

Excessive Production of Glucocorticoid in the Body and the Avoidance of Side Effects in Glucocorticoid Therapy Like in skin fibroblasts, glucocorticoids also stimulate aromatase expression in osteoblasts (Shozu 1998, Tanaka 1996). According to established scholarship opinion, this should properly be favourable for bones. However, clinical experience clearly shows that the systemic treatment with glucocorticoids leads to an all too soon osteoporosis (Jardinet 2000, Lespessailles 2000). This is well explained by the considerations made above, but not by the established scholarship opinion.

An abnormal, excessive production of glucocorticoids in the body, or a therapy with glucocorticoids affects in an undermining manner other components of the connective tissue. The collagen fibres in the skin have already been mentioned in connection with the stretched strias in M. Cushing. The correlation between the stability of tendons and ligaments, which essentially consist of collagen fibres, and glucocorticoids becomes also clear. During glucocorticoid therapy, tendons disrupt more often (Leppilahti 1998). Since glucocorticoids stimulate the expression of aromatase, it is plausible that the vulnerability of tendons such as the Achilles tendon is exerted via this mechanism. Glucocorticoids result, via a decrease of collagen synthesis in the skin, in an atrophy thereof (Oikarinen 1998). It is plausible that this is at least partially based on the stimulus of aromatase expression in skin fibroblasts, so that the accompanying, optionally topical or systemic inhibition of aromatase according to the present invention is capable of avoiding the disadvantageous effects of a therapy with glucocorticoids, in any case those side effects which affect the skin and the connective tissue.

Myocardial Infarction, Brain Infarction and Arteriosclerotic Plaques

Already in the childhood, it occurs that lipids are deposited at the inner wall of arteries. These whitish lipids form together with macrophages, which are partially contained therein, a so-called "fatty streak". It predominantly consists of cholesterol esters. Arteriosclerotic plaques may develop from this "fatty streak" in the course of time (Schwartz 1993). This is a relatively large protrusion within the intimae which is surrounded by a capsule of collagen fibres and consists in the interior of amorphous cholesterol esters and living or dead macrophages (Libby 2000). As long as the collagen fibre capsules are intact, the arteriosclerotic plaque is clinically not noticeable. However, if it disrupts, the blood comes in contact with its content which may quickly cause an intravasal hemostasis with a subsequent fibrinogenic thrombus. This thrombus may then block the artery vessel and thereby stop oxygen delivery for downstream tissue regions and therefore may result in myocardial infarction or brain infarction. The capsule disrupts the easier the thinner it is, the less viscous the content of the plaques is, and the more macrophages the plaques contain which may secerne the collagen digesting enzymes (Libby 1996, Davies 1994). An important therapeutic aim according to the present invention is the stabilization of the plaques. It is less important to decrease the size of the plaques, but to lower their cell and lipid content as far as possible and thus to stabilize them.

An important cause for the drastical increase of myocardial infarctions after the menopause may be that the aromatase in the vessel wall, in particular the macrophages of the plaques, is stimulated by the permanently increased LH concentrations, and that the produced estrogens influence the collagen metabolism of the plaques such that it becomes instable. In fact, the smooth muscle cells of the artery walls contain quite an amount of aromatase (Harada 1999). The coronary arteria can synthesize estradiol and have estrogen receptors (Diano 1999). An inhibition of aromatase, or a blocking of estrogen receptors therefore does not only have a protective effect on the bones, but also on the arteriosclerotic plaques and therefore may help to lower the risk of myocardial infarctions, particularly in postmenopausal women.

Urinary Incontinence

Within four weeks after sterilization, big female dogs often get urinary incontinence (Arnold 1997). This is also a frequent problem of elder women (Distler 2000). This effect is explained for dogs that the mucous membrane of the urinary passageways underlies similar cyclic variations of their constructions by sexual hormones like the mucous membrane of the uterus. It is to be assumed that the dog is in the status of anoestrus for half a year, that is the estrogen production within the ovaries is not stimulated most of the time. Therefore, it is questionable as to how the estrogens may contribute to urinary incontinence. Estrogen therapy does not have a clear improving effect (Jackson 1999). Possibly, there are further hormones from the ovary and the hypothalamus or the pituitary gland which mutually influence each other and which may partially stimulate the local estrogen synthesis.

Since the thickness of the wall of the urethral passageways and therefore possibly also the closure mechanism should depend on a sufficient proportion of collagen fibres, the treatment of urinary incontinence in older women by means of the use of substances inhibiting the production or effects of estrogens according to the present invention, such as the systemic therapy with aramotase inhibitors, is indicated.

The systemic therapy with an aromatase inhibitor having low side effects would have the additional advantage, contrary to the hormone replacement therapy, that the coagulation system is not negatively influenced and that a hemorrhage of the mucous membrane of the uterus is prevented.

Excessive Production of Vitamin D and "After Sun"-Application

Besides glucocorticoids, the expression of aromatase may also be stimulated by fibroblasts and keratinozytes of the skin (Hughes 1997). Vitamin D is formed in the skin by means of exposure to sun irradiation. Therefore, it is plausible that sunbathing decreases the collagen content of the skin.

Therefore, a further useful use of the present invention is to treat at least the exposed parts of the body with a topical application of the substance inhibiting the production or effect of estrogens in order to retard the accelerated formation of wrinkles. This is suitably carried out, in an "after sun" application, after the light or sun exposure which occurred during the day, such as in a topical formulation for the night. The topical formulations which have already been described for the skin applications are suitable, wherein the aromatase inhibitors, and in this connection especially the soya steroles and their analogs, are again preferred due to the proper capability of being absorbed by the skin. Again, from counteracting virilizing effects, the concurrent inhibition of both the aromatase and the 5-alpha-reductase is advantageous.

Influencing Hair Growth in Men and Women

Since the 5-alpha-reductase, and, by the way, both iso enzymes, can be completely inhibited in the skin, it is possible to exhibit by this measure, and by means of concurrently inhibiting aromatase, an influence on the rate of hair growth of the body hair in men and women. The 5-alpha-reductase is also responsible for the boldness formation in men. This is ascertained, because it is possible to stimulate the hair growth on the scalp or to slow down hair loss by means of a systemic administration of Finasterid (Whiting 1999, Brenner 1999). Minoxidil increases the activity of 17-beta-HSD within the scalp, whereby the re-conversion of testosterone into androstendione is enhanced. At the same time, however, 5-alpha-reductase is stimulated (Sato 1999). Finasterid and the anti-androgen flutamid lend themselves for a topical administration on the hair-loosing head. This was successfully performed until now with a scalp model which was transplanted onto nude mice (Sintov 2000) and at the flank organ of gold hamster in order to stop sebaceous gland production there (Chen 1998). Also other 5-alpha-reductase inhibitors were topically well effective there (Chen 1998). Topical administrations of Finasterid and an inhibitor of the type I enzyme were also tested in another sebaceous gland model, namely the male fuzzy rat. Finasterid was little more effective than MK 386. Both substances had much lower effects than an anti-estrogen receptor blocker (RU58841) (Ye 1997). A substance which inhibits the 5-alpha-reductase and, at the same time, acts as an anti-estrogen (4-MA) was applied to the head of monkeys over a period of 27 weeks. The treated monkeys did not have any signs of a boldness, contrary to the untreated individuals (Rittmaster 1987).

That a topical application of a 5-alpha-reductase inhibitor in cases of an excessive hair formation was hitherto not contemplated is clear from the situation that Finasterid, which is an agent for treating prostate hypertrophy, must be administered systemically, in order to achieve the desired effects on the scalp. Finasterid is also administered systemically for the treatment of hirsutism (Muderis 2000).

According to the present invention it was found that the hair growth in women in the face and on the legs after epilation can be significantly slowed down by the concurrent inhibition of aromatase and 5-alpha-reductase. A combination is also advantageous in view of the situation that the production of estrogens in the skin would increase in the skin of the extremities, if 5-alpha-reductase would be inhibited alone. In addition, testosterone, which inhibits aromatase, would be diminished faster (it is converted to dihydrotestosterone). The thus increased production of estrogen in the skin would make it more thin and, at the same time, would increase the subcutaneous fatty tissue. Therefore, it is reasonable to inhibit aromatase at the same time.

Depending on the type of 5-alpha-reductase which is inhibited in addition to the aromatase, the desired hair growth effect can be realized. For example, with an additional inhibition of both types of 5-alpha-reductase, such as with a sterol (4-hydroxy-androstendione) which is very similar to androstendione, possibly not only an inhibition of the growth of the beard, but also of the cutic hairs and of the axillary hairs can be achieved.

EXAMPLES

The invention will be explained by some examples in the following.

Example 1

Ointment for Eye Wrinkles (25 ml)

cetylsteryl alcohol 3.5 ml
natriumlauryl sulfate 0.75 ml
paraffin having low viscosity 5.0 ml
white vaseline 15.5 ml
oxydized soja glycine having
aromatase inhibitory action 0.15 ml 1.1 A 60-year-old man with a strongly expressed wrinkle formation in the eye region, especially at the upper and the lower eyelid:
   After a ten week treatment once per day, a smoothening in the area of the eyelids, and an almost disappearance of the wrinkles occurs.
1.2 A 50-year-old woman with strong wrinkle formation around the eyes, a status 5 years after a lifting treatment.
   Application of the composition of example (1) two times per day:
   Already after eight weeks of treatment, there is a strong smoothening of the upper skin in the region of the wrinkle formation around the eyes; after sixteen weeks, the wrinkles have disappeared such that the woman indicates that she has a better appearance than after the lifting procedure.

Example 2

Cream for the Face (50 ml)

propylene glykole 12.5 ml
isopropyl myristate 3.0 ml
sorbitane monostorate 0.5 ml
Polysorbate 80 1.0 ml
stearyl alkohol 1.0 ml
cetylsteoryl alcohol 3.0 ml
glycerol monostearate 0.5 ml
oxydized soja glycine having
aromatase inhibitory action 0.25 ml
aqua dest. ad 50.0 ml
A 47-year-old woman, strong formation of wrinkles in the lower region of the face, especially in the region of the cheek and the chin:
After six weeks of treatment twice a day with the composition of example 2, a smoothening of the wrinkles was noticeable and visible; after 12 weeks, only slight wrinkles were visible.

Example 3

Cream Lotion of the Upper Arm (100 ml)

Figure 1:
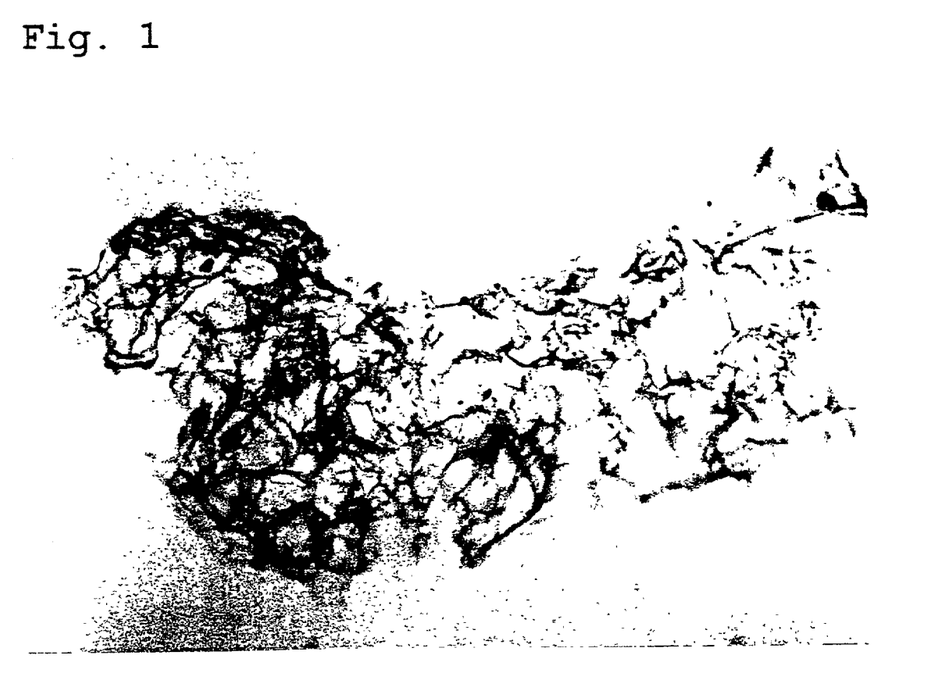
FIG. 1 is a micropyaph of a biopsy before the treatment described in Example 3.
Figure 2:
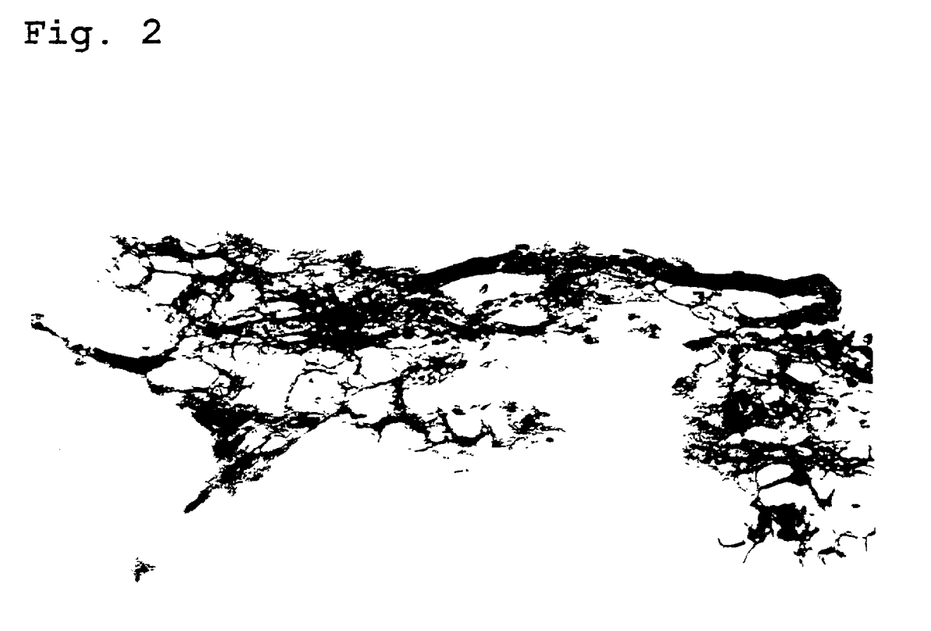
FIG. 2 is a micrograph of a biopsy after treatment of 16 weeks as described in Example 3.

Span 80 1.0 ml
Span 60 5.0 ml
Tween 60 9.0 ml
propylene glykol 15.0 ml
palmitinic acid 9.0 ml
oxydized soja glycine having
aromatase inhibitory action 0.4 ml
aqua dest. ad 100.0 ml
A 43-year-old woman with wrinkles in the outer skin layer of the upper arms; treatment two times a day with the cream lotion: after 4 weeks, a remarkable smoothening is noticeable; after 8 weeks, a clear smoothening is noticeable and visible; after 12 weeks, the wrinkles are strongly reduced; after 16 weeks, wrinkles are practically invisible. (Biopsies before and after the treatment show in micrographs the increase of collagen fibres within the skin: FIG. 1 before the treatment, FIG. 2 after a treatment of 16 weeks.)

Example 4

Gel for Stretched Strias or Pregnancy Strias (100 ml)

microcristalline cellulose 4.0 ml
polyethylene glykol 400 5.0 ml
cetyl alcohol 10.0 ml
oxydized soja glycine having
aromatase inhibitory action 0.4 ml
aqua dent. ad 100.0 ml 4.1 A 27-year-old woman, mother of two children and having strong pregnancy strias in the region of the abdomen; application of the gel-cream 2 times a day.
  Findings: after 6 weeks, a slight smoothening is noticeable; after 12 weeks, the pregnancy strias are strongly reduced; after 18 weeks, no pregnancy strias are visible any more.

Figure 3:
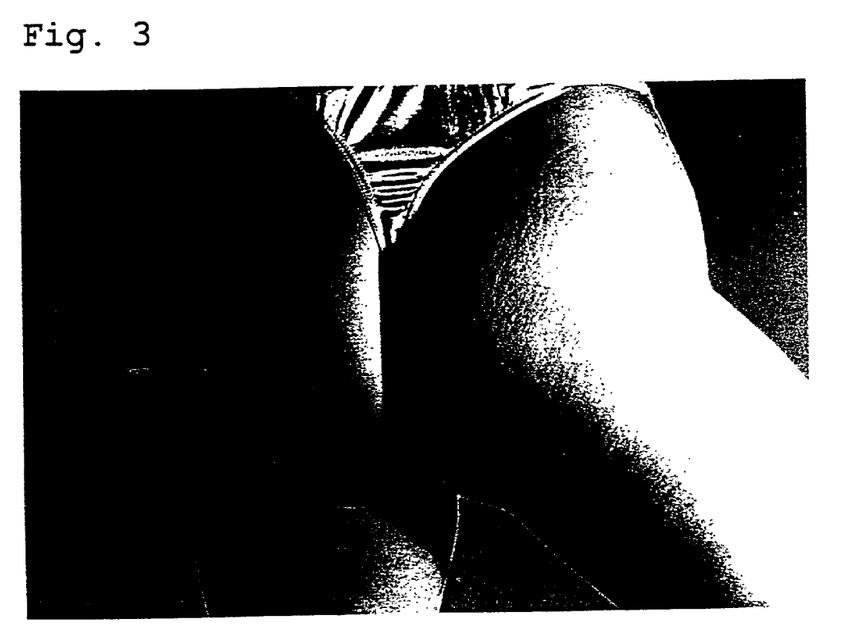
FIG. 3 depicts a woman before the treatment described in Example 4.2.
Figure 4:
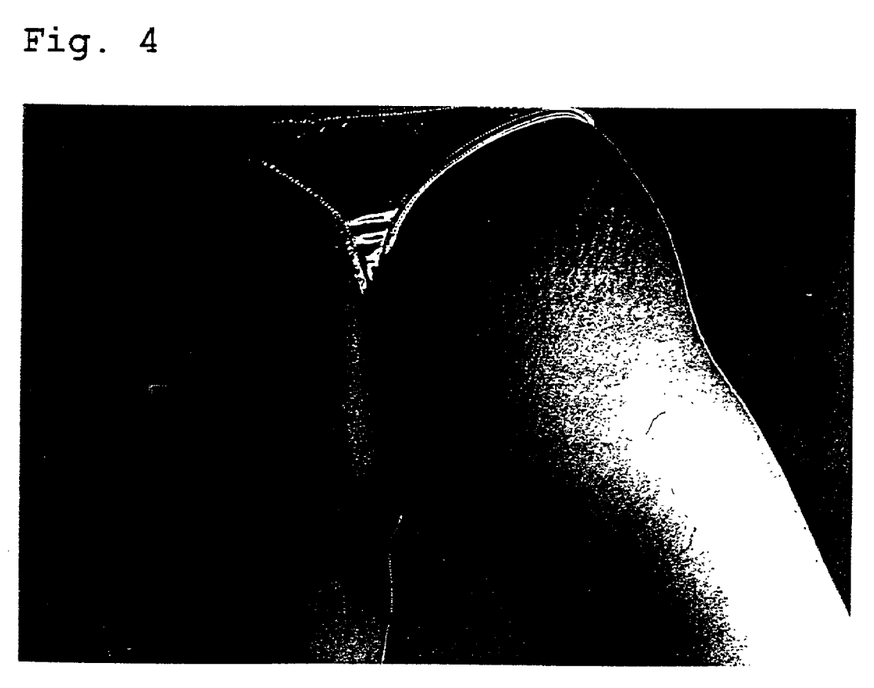
FIG. 4 depicts a woman after treatment of 10 weeks as described in Example 4.2.

4.2 A 25-year-old woman after multiple diets; stretched strias in the region of thighs and buttock. Findings: after 5 weeks, reduction of stretched strias especially at the thighs; already after 10 weeks, reduction, the stretched strias on the thighs and the buttock being (almost) diminished; after 15 weeks, all stretched strias are practically not visible any more: FIG. 3 before the treatment and FIG. 4 after 10 weeks of treatment.

Example 5

Injection Formulation for the Intrafocal Administration (1 ml)

15 mg 4-hydroxy-androstendionee (Formestan)
Auxiliary agents: benzyl alcohol, carmellose-Nd, polysorbate, natrium chloride, water A 30-year-old female tennis player (federal league) having the appearance of strong overstretchings in the joints of both knees (ligaments and tendons), strong pain; playing tennis being only possible with bandages on both sides and undergoing medical treatment with non-steroidal anti-inflammatory substances (NSAID). Injection of the composition of example 5) into the joints of the knee with 2 weeks intervals over a period of 10 weeks: after the 3$^{rd}$. injection (4 weeks), there is already a remarkably reduced NSAID-consumption; after 10 weeks, playing practically without pain (without NSAID!) being possible, there is a feeling of stabilization of the joints of the knees.

Literature:
Arnold S, Schweiz Arch Tierheilkd 1997: 139(6):271-6
Benson J R et al., Br J Cancer 1996 August; 74(3):352-8
Berkovitz G D et al., J Clin Endocrinol Metab 1984 October: 59(4):665-71
Berkovitz G D et al., J Clin Endocrinol Metab 1988 May: 66(5):1029-36
Berkovitz G D et al., Mol Cell Endocrinol 1990 Mar. 5; 69(2-3):187-97
Berkovitz G D et al., J Clin Endocrinol Metab 1992 March: 74(3):629-34
Bisat T et al., In Vitro Cell Dev Biol 1989 September: 25(9): 806-12
Borel J P et al., Pathol Biol (Paris) 1984 September: 32(7): 795-812
Brenner S and Matz H, Int J Dermatol 1999 December: 38(12):928-30
Brodie A M et al., Cancer Res 1989 Dec. 1; 49(23):6551-5; Published erratum appears in Cancer Res 1990 Jan. 15: 50(2):449
Cassidenti D L et al., Obstet Gynecol 1991 July; 78(1):103-7
Chen C et al., J Invest Dermatol 1998 August; 111(2):273-8
Chen W et al., Dermatology 1996; 193(3):177-84
Chen C et al., J Invest Dermatol 1995 November: 105(5):678-82
Courchay G et al., Skin Pharmacol 1996: 9(3):169-76
Cummings S R et al., JAMA 1999 Jun. 16: 281(23):2189-97
Davies M J et al., Basic Res Cardiol 1994: 89 Suppl 1:33-9
de Loes M et al., Scand J Med Sci Sports 2000 April: 10(2): 90-7
Diann S et al., Menopause 1999 Spring: 6(1):21-8
Dijkstra A C et al., J Invest Dermatol 1987 July: 89(1):87-92
Distler W, Z Arztl Fortbild Qualitatssich 2000 April: 94(3): 211-5
Fujimoto M et al., J Clin Endocrinol Metab 1986 August: 63(2):468-74
Gottlieb B et al., Am J Med Genet. 1999 December 29: 89(4):210-7
Gips H et al., J Endocrinol Invest 1980 January-March: 3(1): 51
Grino P B et al., Endocrinology 1990 February: 126(2):1165-72
Hamada K et al., J Invest Dermatol 1996 May: 106(5):1017-22
Harada N, Biochem Biophys Res Commun 1992 Dec. 15: 189(2):1001
Harada N et al., Circ Res 1999 Jun. 11: 84(11):1285-91
Hsiang Y H et al., J Steroid Biochem 1987 January: 26; (1):131-5
Hughes S V et al., Endocrinology 1997 September: 138(9): 3711-8
Iida S et al., J Clin Endocrinol Metab 1991 July: 73(1):192-6
Itami S et al., J Dermatol Sci 1994 July; 7 Suppl:S98-103
Jackson S et al., Br J Obstet Gynaecol 1999 July: 106(7): 711-8
Jardinet D et al., Rheumatology (Oxford) 2000 April: 39(4): 389
Kwan G et al., Kidney Int 1996 October: 50(4):1173-9
Labrie F et al., Ann Endocrinol (Paris) 1995: 56(1):23-9
Labrie F, Mol Cell Endocrinol 1991 July: 78(3):C113-8
Labrie F et al., J Clin Endocrinol Metab 1997 August: 82(8): 2403-9
Lachgar S et al., J Investig Dermatol Symp Proc 1999 December: 4(3):290-5
Lee K S et al., Clin Exp Dermatol 1994 July: 19(4):285-8
Leppilahti J and Orava S, Sports Med 1998 February: 25(2): 79-100
Lespessailles E et al., Joint Bone Spine 2000: 67(2):119-26
Libby P et al., Curr Opin Lipidol 1996 October: 7(5):330-5
Libby P, J Intern Med 2000 March: 247(3):349-58
Luu-The V et al., Invest Dermatol 1994 February: 102(2): 221-6
Mestayer C et al., J Clin Endocrinol Metab 1996 May: 81(5): 1989-93
Marttunen M B et al., Calcif Tissue Int 1999 November: 65(5):365-8
Milewich L et al., Placenta 1990 March-April: 11(2):95-108
Milewich L et al., Ann N Y Acad Sci 1988: 548:66-89
Muderris I I et al., Fertil Steril 2000 May: 73(5):984-7
Nawata H et al., J Steroid Biochem Mol Biol 1995 June: 53(1-6):165-74
Neugarten J et al., Am J Physiol 1999 December: 277(6 Pt 2):F875-81
Oikarinen A et al., Br J Dermatol 1998 December: 139(6): 1106-10
Powell J W and Barber-Foss K D, Am J Sports Med 2000 May-June: 28(3):385-91

Rittmaster R S et al., J Clin Endocrinol Metab 1987 July; 65(1):188-93
Roberts A J et al., Crit. Rev Eukaryot Gene Expr 1995: 5(2): 157
Sasano H et al., Endocr J 1999 April; 46(2):233-42
Sato T et al., J Dermatol Sci 1999 February; 19(2):123-5
Schwartz C J, Am J Cardiol 1993 Feb. 25: 71(6):9B-14B
Sciore P et al., J Orthop Res 1998 September: 16(5):604-10
Setnikar I et al., Arzneimittelforschung 1999 August: 49(8): 708-15
Shozu M and Simpson E R, Mol Cell Endocrinol 1998 Apr. 30: 139 (1-2):117-29
Silbiger S et al., Kidney Int 1999 April: 55(4):1268-76
Sintov A et al., Int J Pharm 2000 Jan. 20: 194(1):125-34
Stanczyk F Z et al., J Steroid Biochem Mol Biol 1990 September; 37(1):129-32
Svenstrup B et al., J Steroid Biochem 1990 May: 35(6):679-87
Tamaoka Y, Nippon Sanka Fujinka Gakkai Zasshi July 1987: 39(7):1129-36
Tanaka S et al., Endocrinology May 1996: 137(5):1860-9
Thiboutot D et al., J Invest Dermatol September 1998: 111 (3):390-5
Theintz G E et al. Horm Res 1989: 32(4):124-9
Whiting D A et al., J Investig Dermatol Symp Proc 1999 December: 4(3):282-4
Wojtys E M et al., Am J Sports Med 1998 September-October: 26(5):614-9
Venencie P Y et al., Br J Dermatol 1999 September: 141(3): 438-46
Winkler E M et al., Am J Phys Anthropol 1993 October: 92(2):155-64
Ye F et al., Skin Pharmacol 1997; 10(5-6):288-97
You S et al., Biol Reprod 2000 January: 62(1):108-16;
Zhao Y et al., Mol Endocrinol 1995 March: 9(3):340-9;

The invention claimed is:

1. A cosmetic treatment comprising the steps of:
   identifying a subject suffering from a condition selected from the group consisting of wrinkles in the face, wrinkles at open-necked regions, pregnancy strias, and stretched strias on the lower abdomen, thighs or buttocks; and
   administering a pharmaceutical composition comprising a steroidal aromatase inhibitor which also has 5-alpha-reductase inhibitor activity to said subject in an amount sufficient to alleviate at least one symptom of said condition wherein said steroidal aromatase inhibitor which also has 5-alpha reductase inhibitor activity is 4-hydroxyandrostenedione or a derivative thereof.

2. The cosmetic treatment method of claim 1, wherein the steroidal aromatase inhibitor is 4-hydroxyandrost-4-ene-3, 17-dione.

3. The cosmetic treatment method of claim 1, wherein the pharmaceutical composition comprises between about 0.001 and about 5% by weight of said steroidal aromatase inhibitor.

4. The cosmetic treatment method of claim 2, wherein the pharmaceutical composition comprises between about 0.001 and about 5% by weight of said steroidal aromatase inhibitor.

5. The cosmetic treatment method of claim 3, wherein the pharmaceutical composition is topically administered.

6. The cosmetic treatment method of claim 4, wherein the pharmaceutical composition is topically administered.

7. The cosmetic treatment method of claim 1, wherein the steroidal aromatase inhibitor is 4-acetyoxy-4androstene-3, 17-dione.

* * * * *